US010365211B2

(12) United States Patent
Blasenheim et al.

(10) Patent No.: US 10,365,211 B2
(45) Date of Patent: Jul. 30, 2019

(54) SYSTEMS AND METHODS FOR METROLOGY BEAM STABILIZATION

(71) Applicant: KLA-Tencor Corporation, Milpitas, CA (US)

(72) Inventors: Barry Blasenheim, Campbell, CA (US); Noam Sapiens, Cupertino, CA (US); Michael Friedmann, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/033,511

(22) Filed: Jul. 12, 2018

(65) Prior Publication Data

US 2019/0094130 A1    Mar. 28, 2019

Related U.S. Application Data

(60) Provisional application No. 62/563,580, filed on Sep. 26, 2017.

(51) Int. Cl.
*G03F 7/20* (2006.01)
*G01B 11/02* (2006.01)
(Continued)

(52) U.S. Cl.
CPC ............ *G01N 21/211* (2013.01); *G01B 11/02* (2013.01); *G02B 26/08* (2013.01);
(Continued)

(58) Field of Classification Search
CPC ...... G01N 21/21; G01N 21/211; G01N 21/25; G01N 21/27; G01N 21/47; G01N 21/55;
(Continued)

(56) References Cited

U.S. PATENT DOCUMENTS 5,103,082 A * 4/1992 Fonneland ............ G01B 11/272
250/201.1
5,315,111 A * 5/1994 Burns .................... B23K 26/04
219/121.8
(Continued)

FOREIGN PATENT DOCUMENTS

WO    2016-189164 A1    12/2016

OTHER PUBLICATIONS

International Search Report dated Jan. 18, 2019, for PCT Application No. PCT/US2018/052334 filed on Sep. 24, 2018 by KLA-Tencor Corporation, 3 pages.
(Continued)

*Primary Examiner* — Gordon J Stock, Jr.
(74) *Attorney, Agent, or Firm* — Spano Law Group; Joseph S. Spano

(57) ABSTRACT

Methods and systems for measuring a specimen while actively stabilizing an optical measurement beam subject to changes in polarization by a rotating polarizer element are described herein. Movement of a focused measurement beam spot induced by a rotating polarizer element is compensated by actively controlling the position of an optical element in the beam path based on measurements of the focused measurement beam spot. Both feedback and feedforward control schemes may be employed to reduce beam position error. In one aspect, a measurement system includes a rotating optical polarizer, a beam position sensor, and an active beam compensating element in the illumination beam path, the collection beam path, or both. Beam position errors are detected by the beam position sensor, and control commands are communicated to the active beam compensating element to reduce the measured beam position errors.

21 Claims, 9 Drawing Sheets

(51) Int. Cl.
- *G01N 21/21* (2006.01)
- *G02B 26/08* (2006.01)
- *G02B 27/00* (2006.01)

(52) U.S. Cl.
CPC ..... *G02B 26/0816* (2013.01); *G02B 26/0875* (2013.01); *G02B 27/0025* (2013.01); *G02B 27/0075* (2013.01); *G03F 7/70625* (2013.01); *G03F 7/70633* (2013.01); *G01N 2021/213* (2013.01)

(58) Field of Classification Search
CPC ........... G01N 21/8422; G01N 21/9501; G01N 2021/213; G03F 7/70608; G03F 7/70616; G03F 7/70625; G03F 7/70633; G03F 7/70641; G03F 7/7065; G01B 11/02; G01B 11/022; G01B 11/024; G01B 11/06; G01B 11/0616; G01B 11/0641; G01B 11/065; G01B 11/14; G01B 11/22; G01B 11/24; G01B 11/30; G02B 26/08; G02B 26/0808; G02B 26/0816; G02B 26/0825; G02B 26/0833; G02B 26/0841; G02B 26/085; G02B 26/0858; G02B 26/0866; G02B 26/0875; G02B 26/0891; G02B 26/10; G02B 26/101; G02B 26/104; G02B 26/106; G02B 26/108; G02B 26/12; G02B 26/124; G02B 26/125; G02B 26/127; G02B 27/0025; G02B 27/0031; G02B 27/0037; G02B 27/0068; G02B 27/0075; G01J 4/00; G01J 4/02; G01J 4/04; G01J 2004/001; G01J 2004/002; G01J 2004/004; G01J 2004/005; G01J 2004/007; G01J 2004/008

USPC ................. 356/364–370, 399–401, 625–636
See application file for complete search history.

(56) References Cited

U.S. PATENT DOCUMENTS

| | | | |
|---|---|---|---|
| 5,373,359 A * | 12/1994 | Woollam | G01J 3/36 356/328 |
| 5,457,310 A | 10/1995 | Fournier | |
| 5,608,526 A | 3/1997 | Piwonka-Corle et al. | |
| 5,768,001 A | 6/1998 | Kelley et al. | |
| 5,859,424 A | 1/1999 | Norton et al. | |
| 5,877,589 A | 3/1999 | Morgan et al. | |
| 5,923,418 A * | 7/1999 | Clark | G01S 17/66 356/153 |
| 6,429,943 B1 | 8/2002 | Opsal et al. | |
| 6,522,387 B2 | 2/2003 | Mulkens | |
| 6,633,831 B2 | 10/2003 | Nikoonahad et al. | |
| 6,693,272 B2 * | 2/2004 | Adachi | G02B 21/0032 250/216 |
| 6,734,967 B1 | 5/2004 | Piwonka-Corle et al. | |
| 6,816,570 B2 | 10/2004 | Janik et al. | |
| 6,895,075 B2 | 5/2005 | Yokhin et al. | |
| 6,972,852 B2 | 12/2005 | Opsal et al. | |
| 6,985,618 B2 | 1/2006 | Adel et al. | |
| 7,067,763 B2 | 6/2006 | Schramm | |
| 7,095,498 B2 * | 8/2006 | Horie | G01N 21/211 356/364 |
| 7,136,172 B1 * | 11/2006 | Johs | G01B 11/26 356/614 |
| 7,248,375 B2 | 7/2007 | Opsal et al. | |
| 7,321,114 B2 | 1/2008 | Lizotte et al. | |
| 7,333,198 B1 * | 2/2008 | Liphardt | G01N 21/21 356/364 |
| 7,352,453 B2 | 4/2008 | Mieher et al. | |
| 7,463,369 B2 | 12/2008 | Wack et al. | |
| 7,478,019 B2 | 1/2009 | Zangooie et al. | |
| 7,502,101 B2 | 3/2009 | Raymond et al. | |
| 7,715,019 B2 | 5/2010 | Kiers et al. | |
| 7,719,677 B2 | 5/2010 | Rosengaus | |
| 7,734,437 B2 | 6/2010 | Tian et al. | |
| 7,826,071 B2 | 11/2010 | Shchegrov et al. | |
| 7,929,667 B1 | 4/2011 | Zhuang et al. | |
| 7,933,026 B2 | 4/2011 | Opsal et al. | |
| 8,030,631 B2 | 10/2011 | Norton et al. | |
| 8,248,617 B2 | 8/2012 | De Groot et al. | |
| 8,441,639 B2 | 5/2013 | Kandel et al. | |
| 8,570,531 B2 | 10/2013 | Li | |
| 8,699,027 B2 | 4/2014 | Wolf et al. | |
| 9,068,952 B2 * | 6/2015 | Petrenko | G01N 21/8806 |
| 9,404,872 B1 | 8/2016 | Wang et al. | |
| 9,518,866 B2 | 12/2016 | Feitisch et al. | |
| 9,587,977 B2 | 3/2017 | Smith et al. | |
| 9,915,522 B1 | 3/2018 | Jiang | |
| 10,215,712 B2 * | 2/2019 | Wolters | G01N 21/8806 |
| 2006/0202115 A1 * | 9/2006 | Lizotte | B23K 26/04 250/234 |
| 2007/0008534 A1 * | 1/2007 | Lo | G11C 17/143 356/401 |
| 2011/0043791 A1 | 2/2011 | Smilde et al. | |
| 2011/0208342 A1 * | 8/2011 | Den Boef | G03F 7/70266 700/109 |
| 2011/0229830 A1 | 9/2011 | Bhattacharyya et al. | |
| 2011/0310388 A1 | 12/2011 | Hill et al. | |
| 2012/0120396 A1 | 5/2012 | Kandel et al. | |
| 2012/0257200 A1 | 10/2012 | Blasenheim et al. | |
| 2013/0042089 A1 | 2/2013 | Vihn et al. | |
| 2013/0114085 A1 | 5/2013 | Wang et al. | |
| 2013/0141730 A1 | 6/2013 | Quintanilha | |
| 2013/0215404 A1 * | 8/2013 | Den Boef | G01J 3/4412 355/44 |
| 2013/0229661 A1 | 9/2013 | Kandel et al. | |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2014/0375981 A1 | 12/2014 | Wang et al. | |
| 2015/0042984 A1 | 2/2015 | Pandev et al. | |
| 2015/0046118 A1 | 2/2015 | Pandev et al. | |
| 2016/0313179 A1 * | 10/2016 | Liebenberg | G01J 1/4257 |
| 2017/0336329 A1 * | 11/2017 | Li | G02B 26/108 |

OTHER PUBLICATIONS

Kim, B. et al., "Adaptive control of a tilt mirror for laser beam steering," Proceedings of the 2004 American Control Conference, Boston, MA, USA, 2004, pp. 3417-3421 vol. 4.

Bifano T.G. et al., "Microelectromechanical deformable mirrors," in IEEE Journal of Selected Topics in Quantum Electronics, vol. 5, No. 1, pp. 83-89, Jan.-Feb. 1999.

Mitchell, Phillip V., "Fast-steering mirrors improve active beam stabilization," Optoelectronics World, Oct. 2001.

* cited by examiner

SYSTEMS AND METHODS FOR METROLOGY BEAM STABILIZATION

TECHNICAL FIELD

The described embodiments relate to metrology systems and methods, and more particularly to methods and systems for improved measurement resolution with smaller measurement box sizes.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

A lithographic process, as described above, is performed to selectively remove portions of a resist material overlaying the surface of a wafer, thereby exposing underlying areas of the specimen on which the resist is formed for selective processing such as etching, material deposition, implantation, and the like. Therefore, in many instances, the performance of the lithography process largely determines the characteristics (e.g., dimensions) of the structures formed on the specimen. Consequently, the trend in lithography is to design systems and components (e.g., resist materials) that are capable of forming patterns having ever smaller dimensions.

Inspection processes based on optical metrology are used at various steps during a semiconductor manufacturing process to detect defects on wafers to promote higher yield. Optical metrology techniques offer the potential for high throughput without the risk of sample destruction. A number of optical metrology based techniques including reflectometry, ellipsometry, and scatterometry implementations and associated analysis algorithms to characterize device geometry have been described. However, it remains a challenge to preserve a small measurement box size. A small measurement box size is especially important in semiconductor inline product metrology where the area available for metrology targets is minimal. The measurement box size refers to the minimum area on the specimen where measurement results are stable and not affected by edge effects (e.g., due to optical diffraction wings) in optical metrology. Hence, the smaller the measurement box size, the smaller the area required for metrology targets. In the semiconductor industry, where wafer space allocated to metrology targets is limited (often, within the scribe line or even within die), the desired box size specification can be often very challenging, such as 30 μm×30 μm, 10 μm×10 μm, or even smaller.

To shrink the size of the measurement box size the amount of signal information that arises from the area surrounding the measurement target and reaches the detector must be minimized. To minimize undesirable signal contamination, the illumination light must be projected onto the measurement target with a minimum of spillover outside of the measurement target area. Diffraction, aberration, image quality, and other limiting effects must be controlled to achieve a smaller illumination spot size. Despite existing approaches designed to control measurement box size, achieving a small measurement box size specification over the full measurement range is very challenging.

Many optical based measurement systems employ rotating polarizer elements to manipulate the polarization of illumination light provided to a specimen, light collected from the specimen, or both. In practical systems, the input and output faces of polarization optics are not perfectly parallel. This misalignment is commonly referred to as a wedge. In addition, the mechanical bearings employed to constrain the rotational motion of the polarization optics have finite concentricity and runout errors. This causes the polarization optics to wobble about the optical axis of a beam passing through the polarization optics. Wedge errors and rotary bearing errors change the optical path of the beam relative to other optical elements in the system. This manifests itself as beam positioning errors at various critical locations in the optical path. For example, for a spectroscopic ellipsometer system, wedge errors and rotary bearing errors cause misalignment of the optical beam with a polarizer slit, the specimen under measurement, and a spectrometer slit as polarizing elements are rotated. As the measurement spot moves during rotation of polarizing elements, measurement precision, accuracy, and matching among multiple tools suffers.

In an attempt to mitigate these problems, various solutions have been contemplated. In some examples, polarizing optics are manufactured with very small wedge tolerances. However, there are practical, manufacturing limits on achievable wedge error tolerance, particularly within reasonable cost. In addition, even if it were possible to manufacture a polarizer element with zero wedge error, changes in environmental conditions (e.g., temperature) cause the wedge angle to change, resulting in movement of the measurement spot during rotation of the polarizer element.

In some examples, improved rotary bearings are employed to reduce measurement beam movement induced by bearing wobble. Again, there are practical, manufacturing limits on achievable runout error tolerance, particularly within reasonable cost. In addition, even if it were possible to manufacture bearings with perfect concentricity and zero runout, bearing wear causes increasing error over time, particularly over the lifetime of semiconductor metrology tool subject to near constant use.

In some examples, a polarizer optic located in the beam path of a converging beam is tilted to compensate for the wedge error. The tilt of the polarizer optic causes a linear offset of the output beam. At the focal point of the converging beam, the linear offset cancels the angular offset caused by the wedge. This approach is not effective if the beam passing through the polarizer optic is collimated. Also, this approach does not work as well if there are two rotating polarizer optics in the beam path. In addition, this approach is not effective when bearings wear over time or wedge errors change with temperature.

As lithographic and metrology systems are pressed to higher resolutions, measurement box size becomes a limiting factor in maintaining device yield. Thus, improved methods and systems for achieving a small measurement box size associated with a variety of metrology technologies are desired.

SUMMARY

Methods and systems for measuring a specimen while actively stabilizing an optical measurement beam subject to changes in polarization by a rotating polarizer element are described herein. Movement of a focused measurement beam spot induced by a rotating polarizer element is compensated by actively controlling the position of an optical element in the beam path based on measurements of the focused measurement beam spot. By reducing the movement of the measurement beam spot, optical measurements of a semiconductor structure are achieved with a reduced measurement box size.

By actively controlling measurement beam movement induced by a rotating polarizer element, wedge error tolerances on polarizer elements may be increased along with rotary bearing tolerances. This increases design flexibility and reduces cost. In addition, active control of measurement beam movement compensates for effects such as temperature shift and bearing wear. In addition, optical system alignment may be checked while the measurement system is running by monitoring measurement beam location and movement.

In one aspect, a measurement system includes a rotating optical polarizer, a beam position sensor, and an active beam compensating element in the illumination beam path, the collection beam path, or both. Beam position errors induced by the rotary motion of the rotating optical polarizer are detected by the beam position sensor. A computing system communicates control commands to the active beam compensating element, and, in response, the active beam compensating element adjusts a location of the measurement beam to reduce the beam position errors as detected by the beam position sensor.

In some examples, the active beam compensating element is controlled by a computing system based on beam position errors measured by the beam position sensor in a feedback control scheme.

In some examples, the active beam compensating element is controlled by a computing system based on the rotational orientation of a rotating polarizer element in a feedforward control scheme.

In general, both feedback and feedforward control schemes as described herein may be employed simultaneously to reduce beam position error.

In a further aspect, a beam position sensor may be employed to measure wafer tilt and z-position of the wafer under measurement.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for measuring a specimen while actively stabilizing an optical measurement beam subject to changes in polarization by a rotating polarizer element are described herein. Movement of a focused measurement beam spot induced by a rotating polarizer element is compensated by actively controlling the position of an optical element in the beam path based on measurements of the focused measurement beam spot. By reducing the movement of the measurement beam spot, optical measurements of a semiconductor structure are achieved with a reduced measurement box size.

By actively controlling measurement beam movement induced by a rotating polarizer element wedge error tolerances on polarizer elements may be increased along with rotary bearing tolerances. This increases design flexibility and reduces cost. In addition, active control of measurement beam movement compensates for effects such as temperature shift and bearing wear. In addition, optical system alignment may be checked while the measurement system is running by monitoring measurement beam location and movement.

Figure 1:
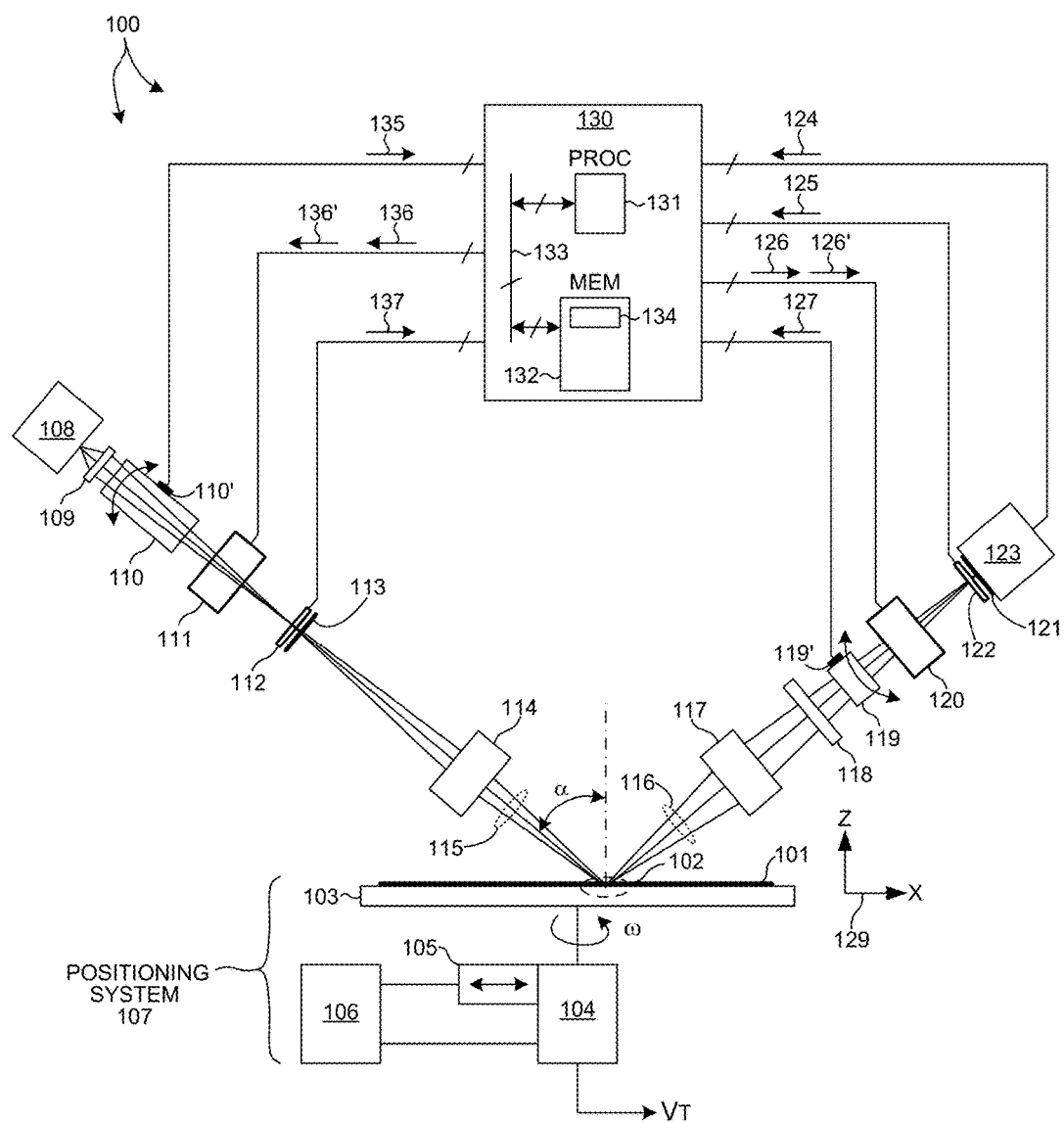
FIG. 1 illustrates an embodiment of a metrology tool 100 for measuring characteristics of a specimen within a small measurement box size.

FIG. 1 illustrates an embodiment of a metrology tool 100 for measuring characteristics of a specimen within a small measurement box size. As depicted in FIG. 1, metrology system 100 may be used to perform optical measurements over a measurement area 102 of a specimen 101 disposed on a specimen positioning system 107.

In general, and as depicted in FIG. 1, metrology tool 100 includes an illumination source 108 and illumination optical elements configured to receive light generated by illumination source 108 and direct illumination measurement beam 115 to the measurement box area 102 of specimen 101. By way of non-limiting example, optical illumination source 108 includes one or more arc lamps, lasers, light emitting diodes, laser driven plasma sources, and laser driven supercontinuum sources, or any combination thereof. In general, any suitable optical illumination source or combination of sources may be contemplated. In some embodiments, optical illumination source 108 is configured to generate illumination light having wavelength components between 100 nanometers and 2500 nanometers.

The illumination optical elements are configured to collimate or focus incident optical illumination beam 115 to measurement box area 102 of specimen 101. In some examples, the illumination optical elements are configured to monochromatize incident illumination measurement beam 115. In some embodiments, the illumination optical elements include one or more optical mirrors, focusing or defocusing optics (reflective or refractive), optical polarization components including polarizers and waveplates, optical apertures, optical monochromators, and optical beam stops, or any combination thereof.

Collection optical elements collect an amount of collected light scattered, reflected, diffracted or refracted from specimen 101 and direct the collection measurement beam 116 to detector 123. Together, the illumination measurement beam and collection measurement beam comprise the measurement beam of the measurement system (i.e., illumination measurement beam 115 and collection measurement beam 116 comprise the measurement beam of metrology system 100). Detector 123 generates output signals 124 indicative of a response of the specimen to the incident illumination light. In some embodiments, scattered optical radiation is detected by optical detector 123 while specimen positioning system 107 locates and orients specimen 101 to produce angularly resolved scattered optical radiation. The optical detector 123 is able to resolve one or more optical photon energies and produces signals for each optical energy component indicative of properties of the specimen. In some embodiments, the optical detector 123 is any of a CCD array, a photodiode array, a CMOS detector or a photomultiplier tube. In some embodiments, optical detector 123 is a spectrometer and measurement data 124 includes an indication of the measured spectral response of the specimen based on one or more sampling processes implemented by an optical spectrometer.

Metrology tool 100 also includes a computing system 130 employed to acquire signals 124 generated by optical detector 123 and determine properties of the specimen based at least in part on the acquired signals. In some embodiments, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference. In general, measurement models associated with not just CD, but also thin film, overlay, pitchwalk, focus/dose, and composition measurements may be applied by computing system 130 to resolve specimen parameter values, by way of non-limiting example. In some other embodiments, computing system 130 is configured to determine properties of the specimen without reference to a physically based reference model, e.g., signal response model based measurements or overlay measurements.

As illustrated in FIG. 1, metrology tool 100 includes a specimen positioning system 107 configured to move specimen 101 under illumination measurement beam 115. In some embodiments, computing system 130 communicates command signals to motion controller 106 of specimen positioning system 107 that indicate the desired position of specimen 101. In response, motion controller 106 generates command signals to the various actuators of specimen positioning system 107 to achieve the desired positioning of specimen 101.

In the embodiment depicted in FIG. 1, specimen positioning system 107 includes a wafer chuck 103, motion controller 106, a rotation stage 104 and a translation stage 105, and a z-stage (not shown). Rotation stage 104 and translation stage 105 are configured to translate specimen 101 in two dimensions within the x-y plane depicted by coordinate system 129. The z-stage is configured to translate specimen 101 in the z-direction depicted by coordinate system 129. Specimen 101 is supported on wafer chuck 103. In some embodiments, specimen 101 is located with its geometric center approximately aligned with the axis of rotation of rotation stage 104. In this manner, rotation stage 104 spins specimen 101 about its geometric center at a specified angular velocity, $\omega$, within an acceptable tolerance. In addition, translation stage 105 translates the specimen 101 in a direction approximately perpendicular to the axis of rotation of rotation stage 104 at a specified velocity, $V_T$. Motion controller 106 coordinates the spinning of specimen 101 by rotation stage 104 and the translation of specimen 101 by translation stage 105 to achieve the desired scanning motion of specimen 101 within system 100.

As depicted in FIG. 1, illumination light generated by illumination source 108 is focused by focusing optics 109 to a focal plane located at or near polarizer slit 113. The illumination beam passes through rotating polarizer 110 (e.g., Rochon polarizer), active beam compensating element 111, and polarizer slit 113. After passing through polarizer slit 113, the polarized beam of illumination light is focused by illumination objective 114 onto specimen 101. A portion of the light reflected, refracted, diffracted, and scattered from the surface of specimen 101 is collected by a collection objective 117. The collection beam 116 is focused by collection objective 117 to a focal plane located at or near spectrometer slit 122. The beam of collected light 116 passes through retarder 118, rotating analyzer 119, active beam compensating element 120, spectrometer slit 122, and is incident on one or more detectors 123 of measurement system 100.

As depicted in FIG. 1, the measurement beam of metrology tool 100 is focused at or near three different intermediate locations: the polarizer slit 113, the wafer 101, and the spectrometer slit 122. Movement of the measurement beam at any of these focal planes negatively impacts measurement precision, accuracy, and repeatability. In the embodiment depicted in FIG. 1, the rotary motion of rotary polarizing element 111 induces movement of the measurement beam at the polarizer slit 113 and wafer 101. In addition, the rotary motion of rotary analyzer 119 induces movement of the measurement beam at the spectrometer slit 122.

Figure 2:
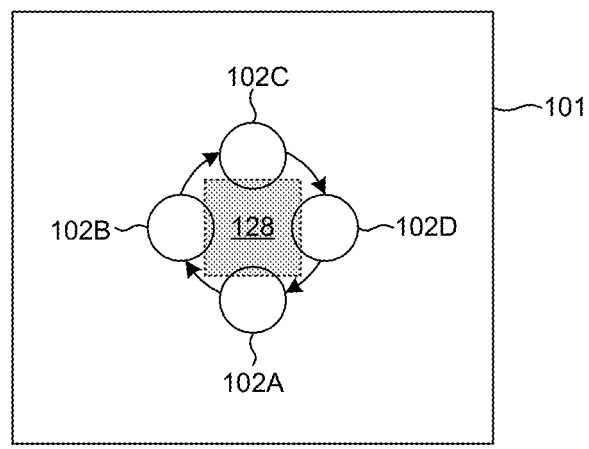
FIG. 2 is a diagram illustrative of a top view of wafer 101 under measurement.

FIG. 2 is a diagram illustrative of a top view of wafer 101 under measurement. A desired measurement area 109 is indicated as a shaded area. In addition, the actual measurement area 102 illuminated by illumination measurement beam 115 is depicted at four different angular orientations of rotating polarizing element 111. As depicted in FIG. 2, wedge errors and rotary bearing errors cause the actual measurement area 102 to move along a trajectory as the angular orientation of rotating polarizing element 111 changes. Four different measurement areas 102A-D are illustrated for four different angular orientations of rotating polarizing element 111. A similar beam positioning error pattern occurs at the focus plane at or near polarizer slit 113.

In one aspect, a measurement system such as metrology system 100 includes a rotating optical polarizer, a beam position sensor, and an active beam compensating element in the illumination beam path, the collection beam path, or both. Beam position errors induced by the rotary motion of the rotating optical polarizer are detected by the beam position sensor. A computing system, such as computing system 130, communicates control commands to the active beam compensating element, and, in response, the active beam compensating element adjusts a location of the measurement beam to reduce the beam position errors as detected by the beam position sensor.

In some examples, the active beam compensating element is controlled by a computing system based on beam position errors measured by the beam position sensor in a feedback control scheme.

In one embodiment, active beam compensating element 111 is controlled by computing system 130 in a feedback control scheme. Beam position sensor 112 detects the position of illumination measurement beam 115 at or near polarizer slit 113. Output signals 137 generated by beam position sensor 112 are communicated to computing system 130. In turn, computing system 130 determines a beam position error (i.e., a difference between the measured beam position and the desired beam position at the particular instance when the beam position is measured. In addition, computing system 130 generates command signals 136 to active beam compensating element 111 that cause active beam compensating element 111 to adjust the beam position and reduce the beam position error.

Similarly, in one embodiment, active beam compensating element 120 is controlled by computing system 130 in a feedback control scheme. Beam position sensor 122 detects the position of collection measurement beam 116 at or near spectrometer slit 121. Output signals 125 generated by beam position sensor 122 are communicated to computing system 130. In turn, computing system 130 determines a beam position error (i.e., a difference between the measured beam position and the desired beam position at the particular instance when the beam position is measured. In addition, computing system 130 generates command signals 126 to active beam compensating element 120 that cause active beam compensating element 120 to adjust the beam position and reduce the beam position error.

In some examples, the active beam compensating element is controlled by a computing system based on the rotational orientation of a rotating polarizer element in a feedforward control scheme. In one example, beam position errors are measured (e.g., by a beam position sensor) as a function of rotational orientation of the rotating polarizer element without active correction as part of a calibration measurement. Based on the measured beam position errors, control commands that reduce the beam position errors are determined as a function rotational orientation. The measured errors, control commands, or both, are stored as a function or in a look-up table in a memory accessible by the computing system. During operation, the orientation of the rotating polarizer element is measured. Computing system determines a control command to reduce beam position errors based on the measured orientation and the stored function or look-up table. Computing system communicates the control command to the active beam compensating element to reduce the beam position errors. In some other examples, calibration measurements may be performed with known error correction as a function of rotational orientation in an iterative manner to arrive at control commands as a function of orientation that minimize beam position errors during operation.

In one embodiment, active beam compensating element 111 is controlled by computing system 130 in a feedforward control scheme. A rotational orientation sensor 110' of rotating polarizer element 110 detects the rotational position of rotating polarizer element 110. Output signals 135 generated by sensor 110' are communicated to computing system 130. In turn, computing system 130 determines a beam position control command 136' based on the measured orientation and a stored function or look-up table at the particular instance when the beam position is measured. In addition, computing system 130 communicates the beam position control command 136' to active beam compensating element 111 that causes active beam compensating element 111 to adjust the beam position and reduce the beam position error.

Similarly, in one embodiment, active beam compensating element 120 is controlled by computing system 130 in a feedforward control scheme. A rotational orientation sensor 119' (e.g., rotary encoder) of rotating polarizer element 119 detects the rotational position of rotating polarizer element 119. Output signals 127 generated by sensor 119' are communicated to computing system 130. In turn, computing system 130 determines a beam position control command 126' based on the measured orientation and a stored function or look-up table at the particular instance when the beam position is measured. In addition, computing system 130 communicates the beam position control command 126' to active beam compensating element 120 that causes active beam compensating element 120 to adjust the beam position and reduce the beam position error.

In general, both feedback and feedforward control schemes as described herein may be employed simultaneously to reduce beam position error.

Figure 3A:
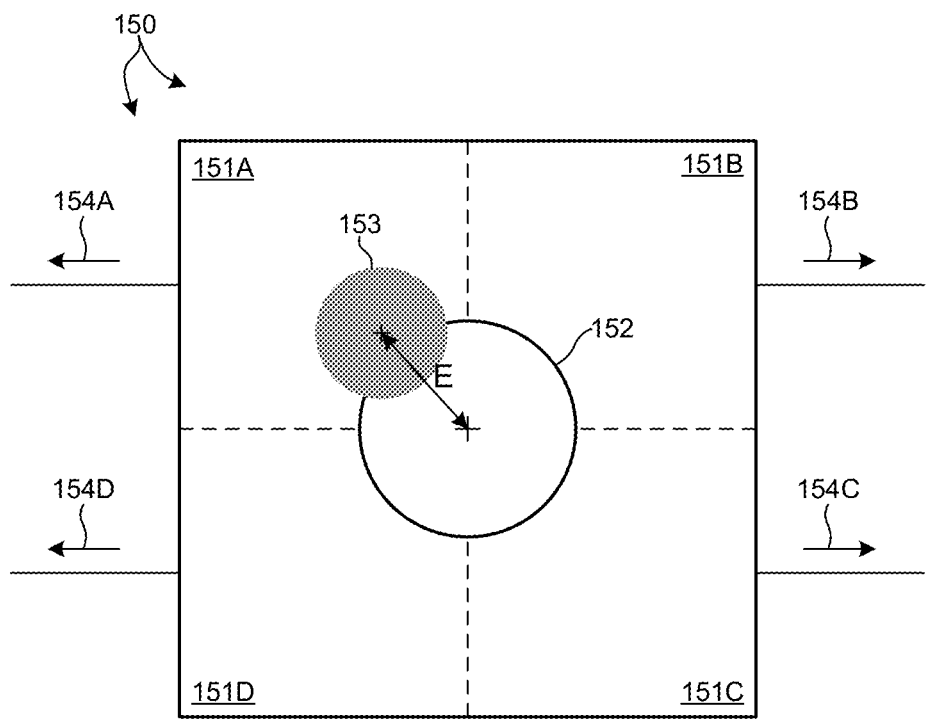
FIG. 3A depicts a measurement beam partially transmitted through an aperture and partially measured by a beam position sensor arranged in quadrature.
Figure 3B:
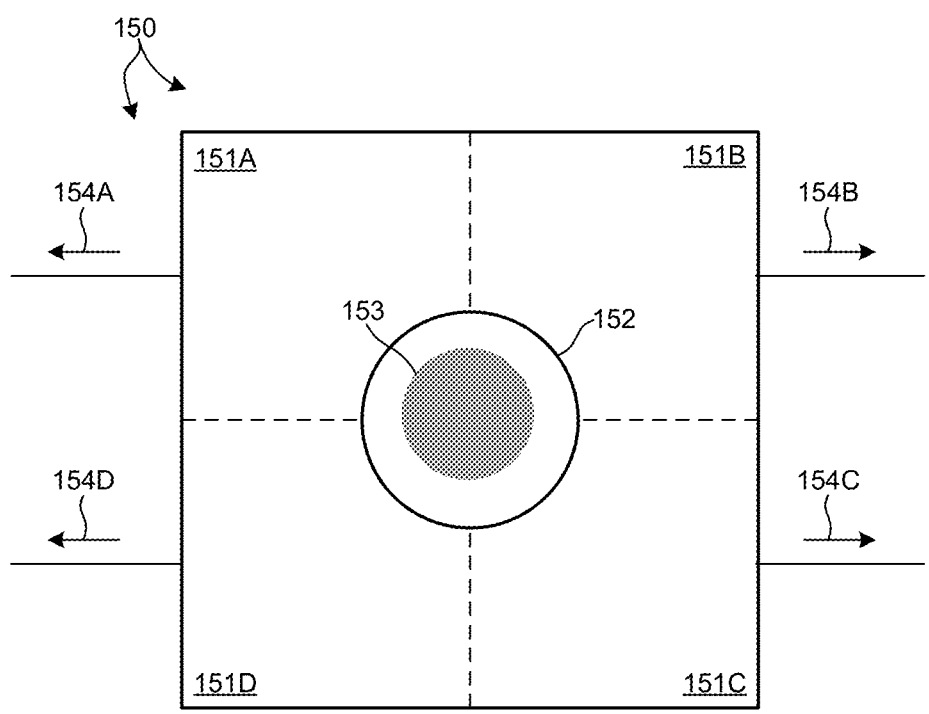
FIG. 3B depicts a measurement beam passing through an aperture after correction by an active beam compensating element.

FIGS. 3A and 3B depict a beam position sensor 150 in one embodiment. Beam position sensor 150 includes four photosensitive elements 151A-D arranged in quadrature. By way of non-limiting example, the photosensitive elements may be any of an array of charge coupled devices (CCD), an array of complementary metal oxide on silicon (CMOS) devices, a position sensitive detector (PSD) device, an array of photomultiplier tubes (PMT), and an array of photodiodes. In addition, beam position sensor 150 includes an aperture 152 in the middle of the quadrature arrangement to allow the measurement beam to pass. As beam position error increases, a portion of the measurement beam 153 is incident on one of the photosensitive elements of beam position sensor 150. For example, as depicted in FIG. 3A, measurement beam 153 is partially transmitted through aperture 152. However, a large portion of measurement beam 153 is incident on photosensitive element 151A. In this example, output signals 154A-D generated by photosensitive element 151A-D indicate the beam position error, E, when beam position errors are below a threshold value. FIG. 3B depicts measurement beam 153 passing through aperture 152 of beam position sensor 150 after correction by an active beam compensating element as described herein (e.g., active beam compensating elements 111 and 120 depicted in FIG. 1). In this instance, the beam positioning errors are below the threshold set by the size of the aperture 152 and output signals 154A-D indicate no beam position error.

In general, a beam position sensor 150 is located as close as practical to a focal plane of a measurement system. For example, a beam position sensor 150 may be located at or near focal planes located at or near polarizer slit 113 and spectrometer slit 121. In practice, it may not be possible to locate beam position sensor 150 exactly at a focal plane (e.g., mechanical interference with polarizer slit 113 and spectrometer slit 121). However, beam position sensor 150 provides sufficient information regarding beam position when the beam position sensor 150 is not perfectly aligned with a focal plane.

Figure 4A:
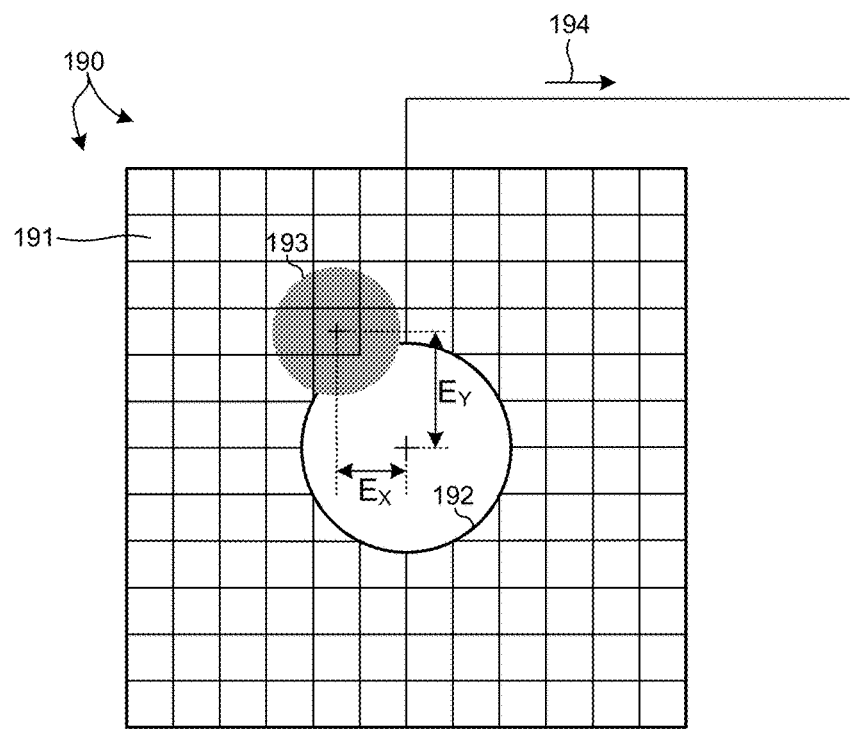
FIG. 4A depicts a measurement beam partially transmitted through an aperture and partially measured by an array of photosensitive elements.
Figure 4B:
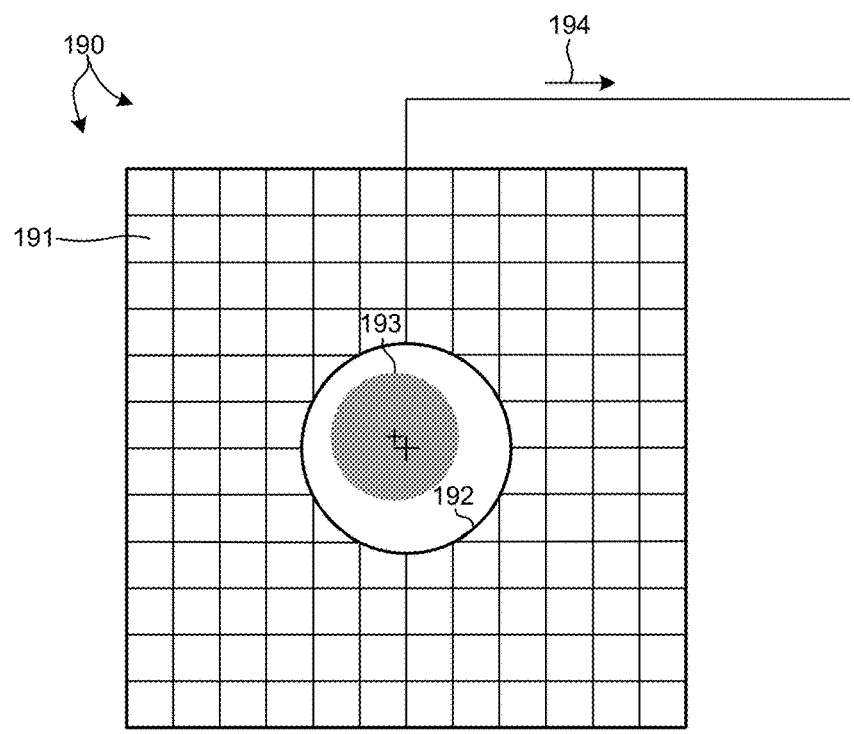
FIG. 4B depicts a measurement beam passing through an aperture after correction by an active beam compensating element.

FIGS. 4A and 4B depict a beam position sensor 190 in one embodiment. Beam position sensor 190 includes an array of photosensitive elements 191 arranged around an aperture 192 that allows the measurement beam to pass. By way of non-limiting example, the photosensitive elements may be any of an array of charge coupled devices (CCD), an array of complementary metal oxide on silicon (CMOS) devices, a position sensitive detector (PSD) device, an array of photomultiplier tubes (PMT), and an array of photodiodes. The array of photosensitive elements 191 may be configured as an integrated array or an array of discrete devices. As beam position error increases, a portion of the measurement beam 193 is incident on one or more of the photosensitive elements of beam position sensor 190. For example, as depicted in FIG. 4A, measurement beam 193 is partially transmitted through aperture 122. However, a large portion of measurement beam 193 is incident on a number of photosensitive elements. In this example, output signals 194 generated by the photosensitive elements indicate the beam position error in two dimensions (i.e., error in the x-direction, $E_x$, and error in the y-direction, $E_y$).

FIG. 4B depicts measurement beam 193 passing through aperture 192 of beam position sensor 190 after correction by an active beam compensating element as described herein (e.g., active beam compensating elements 111 and 120 depicted in FIG. 1). In this instance, the beam positioning errors are below the threshold set by the size of the aperture 192 and output signals 194 indicate no beam position error.

In general, a beam position sensor 190 is located as close as practical to a focal plane of a measurement system. For example, a beam position sensor 190 may be located at or near focal planes located at or near polarizer slit 113 and spectrometer slit 121. In practice, it may not be possible to locate beam position sensor 190 exactly at a focal plane (e.g., mechanical interference with polarizer slit 113 and spectrometer slit 121). However, beam position sensor 190 provides sufficient information regarding beam position when the beam position sensor 150 is not perfectly aligned with a focal plane.

Figure 5:
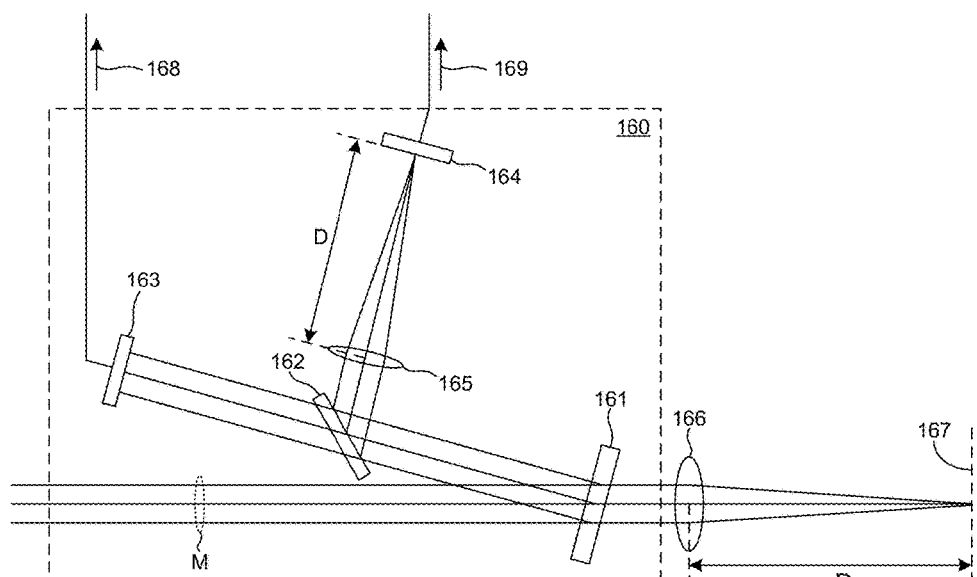
FIG. 5 depicts a beam position sensor 160 in one embodiment.

FIG. 5 depicts a beam position sensor 160 in one embodiment. Beam position sensor 160 includes a beam diversion element 161 in the optical path of the measurement beam, M. Exemplary beam diversion elements include a "pick-off" mirror, such as an uncoated window. A suitable uncoated window may be fabricated from fused silica or Calcium Fluoride. In the example depicted in FIG. 5, the beam diversion element 161 is a tilted, uncoated window. As depicted in FIG. 5, the measurement beam incident on beam diversion element 161 is collimated and the window 161 transmits about 92% of the light. The transmitted light passes through focusing optics 166, which focuses the measurement beam at a focal plane 167 over a focal distance, D. A portion of the light reflected from beam diversion element 161 is reflected by beamsplitting element 162 and focused by focusing optics 165 over focal distance, D, onto beam position detector 164. The movement of the beam on beam position detector 164 is indicative of the beam angle at incidence of focusing optics 165, which matches the beam angle of the measurement beam at incidence of focusing optics 166. Thus, beam position detector 164 generates output signals 169 indicative of the beam angle of the measurement beam at incidence with focusing optics 166.

In a further aspect, light transmitted through beamsplitting element 162 is incident on beam position detector 163. The movement of the beam incident on beam position detector 163 is indicative of the position of the measurement beam (e.g., (x,y) position). Beam position detector 163 generates output signals 168 indicative of the position of the measurement beam. In this manner, beam position sensor 160 detects both beam angle and beam position of the measurement beam. In some embodiments, a measurement system includes an active beam compensating element arranged to correct beam position based on output signals 168 and another active beam compensating element arranged to correct beam angle based on output signals 169. This enables the correction of larger alignment errors than could be accomplished by correcting only beam angle or only beam position.

In general, beam position sensor 160 may be arranged to measure beam angle only, or, alternatively, beam position only. For example, beam position sensor 160 may be arranged to measure beam angle only by replacing beamsplitting element 162 with a mirror and deleting beam position detector 163. In another example, beam position sensor 160 may be arranged to measure beam position only by deleting beamsplitting element 162, focusing optics 165, and beam position detector 164.

By way of non-limiting example, beam position detectors 163 and 164 may be configured as an array of charge coupled devices (CCD), an array of complementary metal oxide on silicon (CMOS) devices, a position sensitive detector (PSD) device, an array of photomultiplier tubes (PMT), and an array of photodiodes.

In a further aspect, beam position sensor 160 may be employed as part of metrology tool 100 to measure wafer tilt and z-position of the wafer under measurement. Beam location measured at beam position detectors 163 and 164 is sensitive to wafer tilt and z-position, in addition to being sensitive to beam errors induced by a rotary polarizing element. In some examples, the beam errors induced by the rotary polarizing elements are largely mitigated by feedforward control based on a calibrated model or look-up table as described hereinbefore. After calibration of the beam errors induced by the rotary polarizing element, additional beam errors detected by beam position detectors 163 and 164 are indicative of wafer tilt and z-position errors. In this manner, output signals 168 and 169 are employed by computing system 130 to estimate z-position errors and wafer tilt during measurement.

Beam position sensor 160 offers advantages as an indicator of z-position errors and wafer tilt because the errors indicative of the z-position errors and wafer tilt are directly measured from the measurement beam of the measurement tool, rather than a separate optical system. This significantly reduces drift and stability issues that arise by measuring z-position errors and wafer tilt by a separate optical system.

FIGS. 6A-6D depict an active beam compensating element 145 in one embodiment. Active beam compensating element 145 includes a moveable mirror element, mirror actuators 142, and driver 141. Command signals 143 are received from a computing system (e.g., computing system 130). In response to the command signals 143, driver 141 controls the motion of actuators 142 employed to located mirror element 140. Suitable actuators include piezoelectric actuators, motorized leadscrews, etc. In some embodiments, the mirror element 140 is coupled to actuators 142 with a kinematic mount to mitigate the potential for mechanical over-constraint and potential deformation of mirror element 140.

Figure 6A:
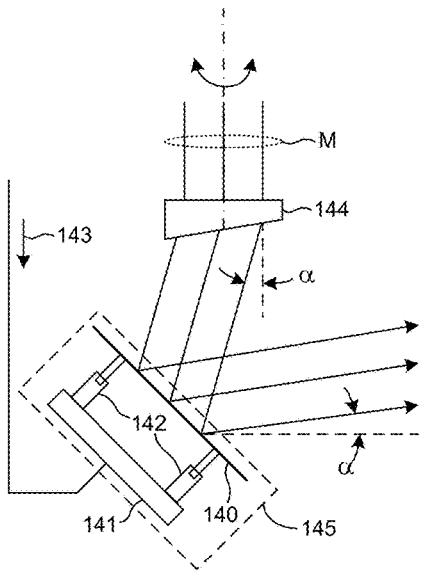
FIG. 6A depicts a beam angle error, $\alpha$, induced by a wedge error without error correction.
Figure 6B:
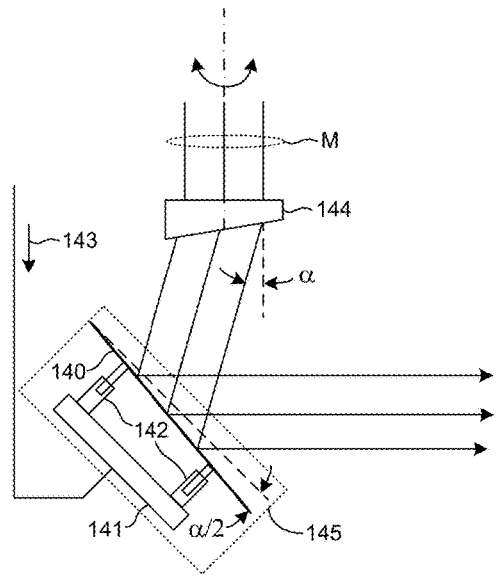
FIG. 6B depicts a beam angle error, $\alpha$, induced by a wedge error with error correction in one embodiment.
Figure 6C:
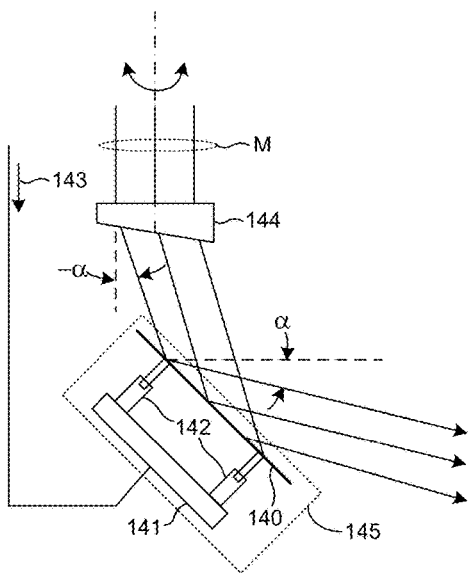
FIG. 6C depicts a beam angle error, $-\alpha$, induced by a wedge error without error correction.
Figure 6D:
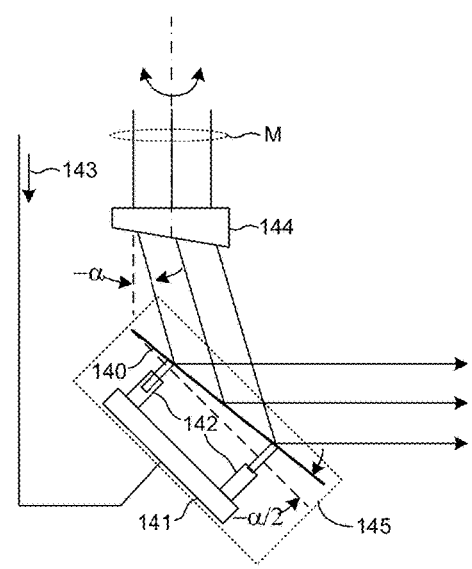
FIG. 6D depicts a beam angle error, $-\alpha$, induced by a wedge error with error correction in one embodiment.

As depicted in FIGS. 6A-6D, active beam compensating element 145 is located in the optical path of measurement beam, M. Measurement beam, M, passes through rotating polarizer element 144 which includes a wedge error. As depicted in FIG. 6A, the wedge error induces a beam angle error, $\alpha$. FIG. 6A illustrates a scenario where no corrective action is taken by the active beam compensating element 145. In this scenario, the beam angle error, $\alpha$, continues to propagate. FIG. 6B illustrates a scenario where active beam compensating element 145 receives command signals 143 that cause the actuators 140 to rotate mirror 140 by an angle, $\alpha/2$. This change of orientation of mirror element 140 compensates for the beam angle error, $\alpha$, induced by the rotating polarizer element 144. FIGS. 6C and 6D depict the rotating polarizer element at an orientation opposite that of FIGS. 6A and 6B. Hence, the wedge error induces a beam angle error, $-\alpha$. FIG. 6C illustrates a scenario where no corrective action is taken by the active beam compensating element 145. In this scenario, the beam angle error, $-\alpha$, continues to propagate. FIG. 6D illustrates a scenario where active beam compensating element 145 receives command signals 143 that cause the actuators 140 to rotate mirror 140 by an angle, $-\alpha/2$. This change of orientation of mirror element 140 compensates for the beam angle error, $-\alpha$, induced by the rotating polarizer element 144.

Figure 7A:
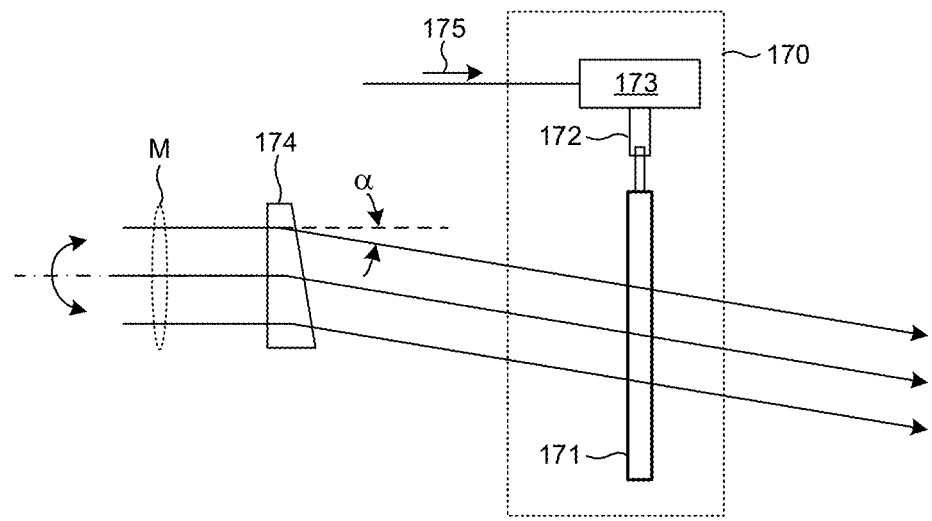
FIG. 7A depicts a beam angle error, $\alpha$, induced by a wedge error without correction.
Figure 7B:
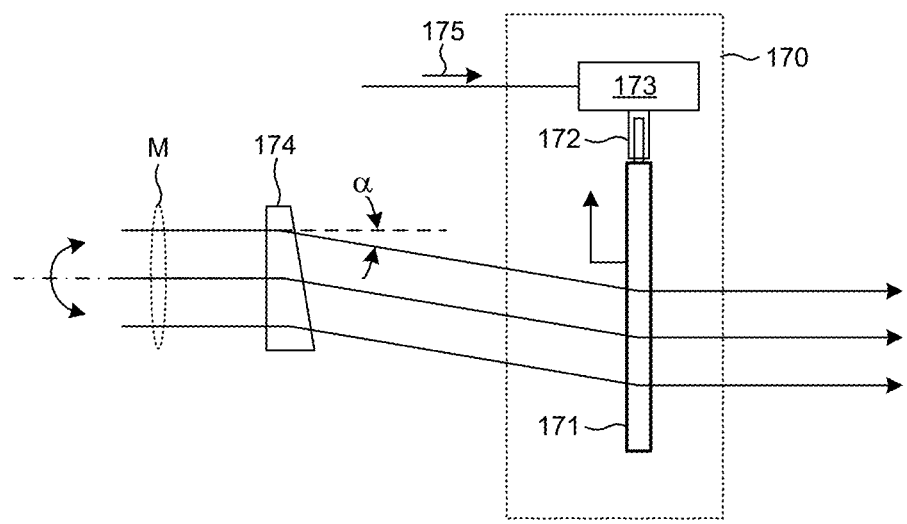
FIG. 7B depicts a beam angle error, $\alpha$, induced by a wedge error with correction in another embodiment.

FIGS. 7A-7B depict an active beam compensating element 170 in one embodiment. Active beam compensating element 170 includes a moveable lens element 171, lens actuators 172, and driver 173. Command signals 175 are received from a computing system (e.g., computing system 130). In response to the command signals 175, driver 173 controls the motion of actuators 172 employed to locate lens element 171. Suitable actuators include piezoelectric actuators, motorized leadscrews, etc. In some embodiments, the lens element 171 is coupled to actuators 172 with a kinematic mount to mitigate the potential for mechanical over-constraint and potential deformation of mirror element 171.

As depicted in FIGS. 7A-7B, active beam compensating element 170 is located in the optical path of measurement beam, M. Measurement beam, M, passes through rotating polarizer element 174 which includes a wedge error. As depicted in FIG. 7A, the wedge error induces a beam angle error, $\alpha$. FIG. 7A illustrates a scenario where no corrective action is taken by the active beam compensating element 170. In this scenario, the beam angle error, $\alpha$, continues to propagate. FIG. 7B illustrates a scenario where active beam compensating element 170 receives command signals 175 that cause the actuators 172 to translate lens element 171 such that the central axis of the lens element is offset from the central axis of beam, M, by a specified amount. This transverse movement of lens element 171 with respect to measurement beam, M, compensates for the beam angle error, $\alpha$, induced by the rotating polarizer element 144.

Figure 8A:
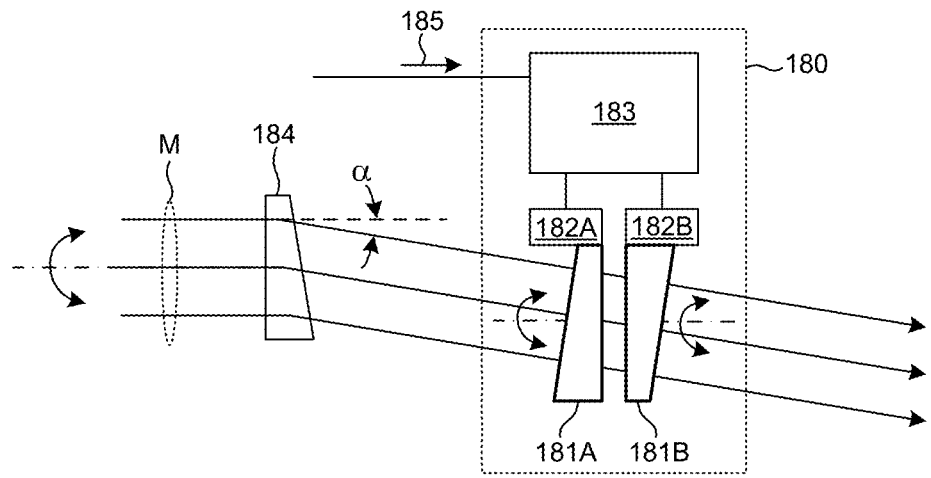
FIG. 8A depicts a beam angle error, $\alpha$, induced by a wedge error without correction.
Figure 8B:
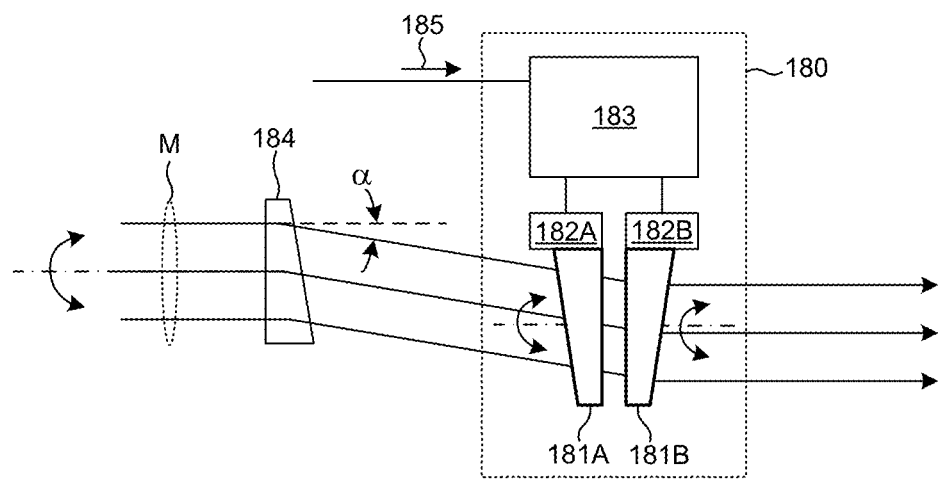
FIG. 8B depicts a beam angle error, $\alpha$, induced by a wedge error with correction in yet another embodiment.

FIGS. 8A-8B depict an active beam compensating element 180 in one embodiment. Active beam compensating element 180 includes two equal but opposite wedged optical elements (e.g., Risley Prisms) 181A and 181B, rotary actuators 182A and 182B coupled to optical element 181A and 181B, respectively, and driver 183. Command signals 185 are received from a computing system (e.g., computing system 130). In response to the command signals 185, driver 183 controls the motion of actuators 182A and 182B employed to locate wedged elements 181A and 181B, respectively.

As depicted in FIGS. 8A-8B, active beam compensating element 180 is located in the optical path of measurement beam, M. Measurement beam, M, passes through rotating polarizer element 184 which includes a wedge error. As depicted in FIG. 8A, the wedge error induces a beam angle error, $\alpha$. FIG. 8A illustrates a scenario where no corrective action is taken by the active beam compensating element 180. In this scenario, the beam angle error, $\alpha$, continues to propagate. FIG. 8B illustrates a scenario where active beam compensating element 180 receives command signals 185 that cause the actuators 182A and 182B to rotate wedge elements 181A and 181B to compensate for the beam angle error, $\alpha$, induced by the rotating polarizer element 144.

Although FIG. 1 depicts a rotating optical polarizer, a beam position sensor, and an active beam compensating element in both the illumination beam path and the collection beam path, in general, a rotating optical polarizer, a beam position sensor, and an active beam compensating element may be located only in the illumination beam path or only in the collection beam path. In general, a beam compensating element and a beam position sensor may be located anywhere in the optical path of the measurement system after a rotating optical polarizer element to correct beam positioning errors induced by the rotating polarizer element. In general, a rotating optical polarizer element includes any rotating optical element that alters the polarization of light transmitted through the optical element. By way of non-limiting example, a rotating optical polarizer element includes any rotating optical polarizer element commonly referred to as a rotating polarizer, a rotating compensator, a rotating retarder, a rotating analyzer, a rotating waveplate, etc.

Figure 9:
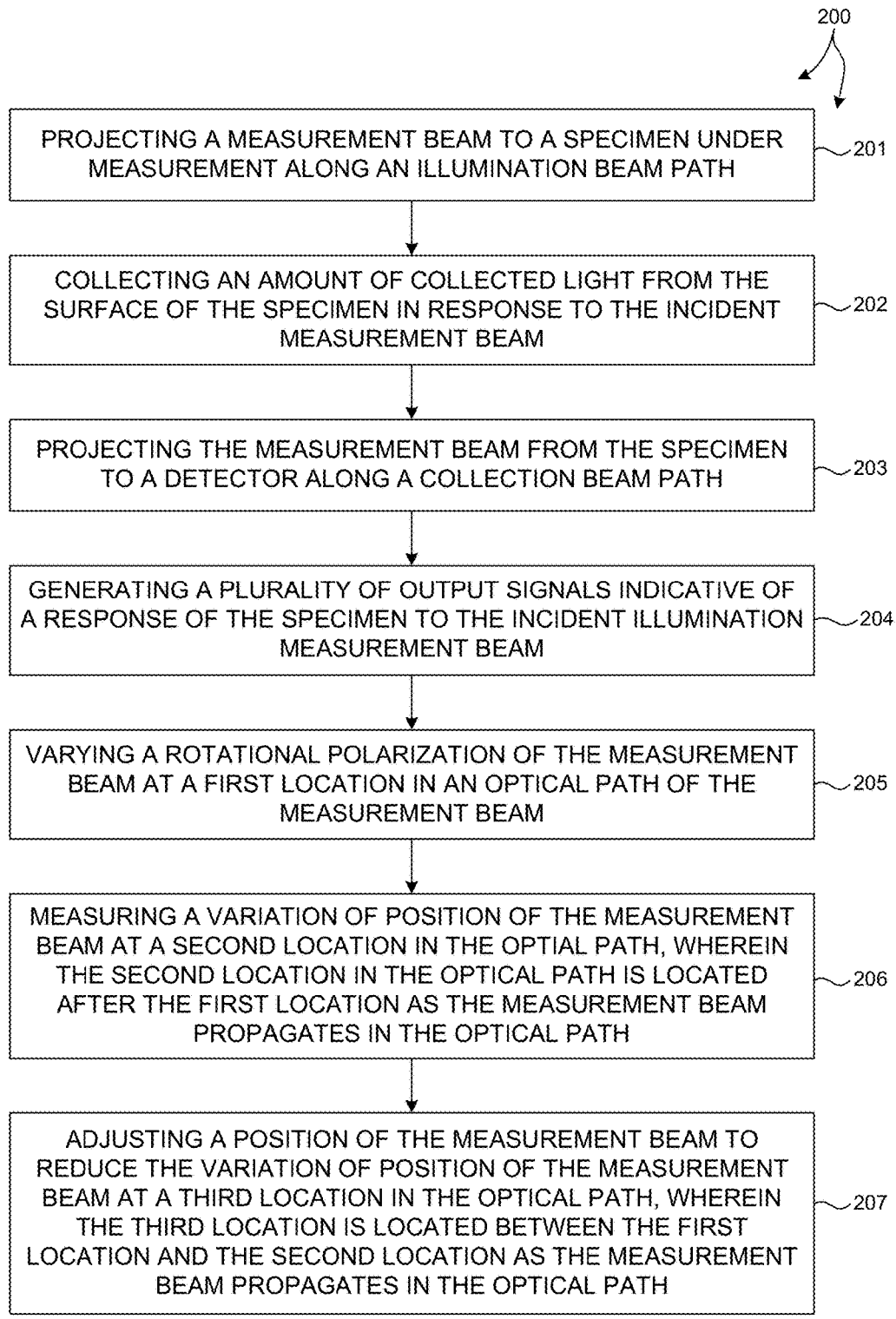
FIG. 9 depicts a flowchart 200 of a method for correcting beam errors induced by rotating polarizer elements as described herein.

FIG. 9 illustrates a method 200 suitable for implementation by a metrology system (e.g., metrology system 100 illustrated in FIG. 1). In one aspect, it is recognized that data processing blocks of method 200 may be carried out via a pre-programmed algorithm executed by one or more processors of computing system 130. While the following description of the method 200 is presented in the context of metrology system 100, it is recognized herein that the particular structural aspects of metrology system 100 do not represent limitations and should be interpreted as illustrative only.

In block 201, a measurement beam is projected to a specimen under measurement along an illumination beam path.

In block 202, an amount of collected light is collected from the surface of the specimen in response to the incident measurement beam.

In block 203, the measurement beam is projected from the specimen to a detector along a collection beam path.

In block 204, a plurality of output signals indicative of a response of the specimen to the incident illumination measurement beam are generated.

In block 205, a rotational polarization of the measurement beam is varied at a first location in an optical path of the measurement beam.

In block 206, a variation of position of the measurement beam is measured at a second location in the optical path. The second location in the optical path is located after the first location as the measurement beam propagates in the optical path.

In block 207, a position of the measurement beam is adjusted to reduce the variation of position of the measurement beam at a third location in the optical path. The third location is located between the first location and the second location as the measurement beam propagates in the optical path.

It should be recognized that various steps described throughout the present disclosure may be carried out by a single computer system 130 or, alternatively, a multiple computer system 130. Moreover, different subsystems of the system 100, such as the specimen positioning system 107, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the optical detector 123, rotating optical polarizer elements 110 and 119, active beam compensating elements 111 and 120, and beam position sensors 112 and 122 in any manner known in the art. For example, the one or more computing systems 130 may be coupled to computing systems associated with the optical detector 123, rotating optical polarizer elements 110 and 119, active beam compensating elements 111 and 120, and beam position sensors 112 and 122. In another example, any of the optical detector 123, rotating optical polarizer elements 110 and 119, active beam compensating elements 111 and 120, and beam position sensors 112 and 122 may be controlled directly by a single computer system coupled to computer system 130.

The computer system 130 may be configured to receive and/or acquire data or information from the subsystems of the system (e.g., optical detector 123, rotating optical polarizer elements 110 and 119, active beam compensating elements 111 and 120, and beam position sensors 112 and 122 160, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 124) from a storage medium (i.e., memory 132 or an external memory) via a data link. In one example, spectral results obtained using a spectrometer of optical detector 123 may be stored in a permanent or semi-permanent memory device (e.g., memory 132 or an external memory). In another example, desired states of active beam compensating elements 111 and 120 as a function of rotational position of rotating optical polarizer elements 110 and 119, respectively, determined by computer system 130, or another computing system may be stored in a permanent or semi-permanent memory device (e.g., memory 132 or an external memory). In this regard, the desired states may be imported from on-board memory or from an external memory system. Moreover, the computer system 130 may send data to other systems via a transmission medium. For instance, desired states of active beam compensating elements 111 and 120 as a function of rotational position of rotating optical polarizer elements 110 and 119, respectively, determined by computer system 130, or another computing system may be stored in a permanent or semi-permanent memory device (e.g., memory 132 or an external memory). In this regard, results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In general, a variety of metrology system architectures benefit from a reduced measurement box size enabled by active compensation of beam motion induced by rotary polarizer elements in the optical path of the measurement beam. In some examples, a small metrology box size is achieved for metrology architectures with multiple angles of incidence using the methods and apparatus described herein. These include but are not limited to multiple-AOI spectroscopic ellipsometry (SE) in its standard or Mueller matrix (MMSE) implementations, multiple-AOI spectroscopic reflectometry, beam profile reflectometry (BPR), single wavelength ellipsometry, beam profile ellipsometry (BPE), with BPR or BPE technologies used in either one-dimensional or two-dimensional angle-resolved implementations, angle resolved scatterometry, and spectroscopic scatterometry.

However, in general the methods and apparatus described herein are compatible with all known optical metrology tools individually, or in combination as part of a combined measurement analysis. Such optical metrology techniques include, by way of non-limiting example, spectroscopic ellipsometry, spectroscopic reflectometry, angle-resolved reflectometry and ellipsometry, spectroscopic scatterometry, scatterometry overlay, beam profile reflectometry, (angle and polarization resolved), beam profile ellipsometry, single or multiple discrete wavelength ellipsometry, multiple angle of incidence ellipsometry, and spectroscopic polarimetry, etc. In general, any metrology technique applicable to the characterization of semiconductor structures, including image based metrology techniques, may be contemplated.

In some examples, the apparatus and methods described herein to achieve a small size measurement box may be used in conjunction with existing focused beam ellipsometer systems such as described by 1) U.S. Pat. No. 5,608,526 entitled "Focused beam spectroscopic ellipsometry method and system," issued Mar. 4, 1997, to KLA-Tencor Corporation, the contents of which are incorporated by reference as if fully set forth herein, and 2) U.S. Pat. No. 5,859,424 entitled "Apodizing filter system useful for reducing spot size in optical measurements and other applications," issued Jan. 12, 1999, to KLA-Tencor Corporation, the contents of which are incorporated by reference as if fully set forth herein.

The methods and apparatus described herein to achieve a small metrology box size are useful for CD metrology, thin film metrology, shape metrology, and composition metrology. However, these applications are not limiting, the methods described herein are also useful in overlay metrology applications, pitchwalk measurement applications, focus and dosage monitoring applications, etch monitoring applications, lithography applications, etc.

In general, the methods and apparatus described in this patent document may also be implemented as part of a fabrication process, and/or fabrication process tool. Examples of fabrication process tools include, but are not limited to, lithographic exposure tools, film deposition tools, implant tools, and etch tools. In this manner, measurement results are used to control a fabrication process. In one example, measurement data collected from one or more targets in accordance with the methods and apparatus described herein is used by a lithography tool to control focus and dosage. In another example, measurement data collected from one or more targets in accordance with the methods and apparatus described herein is used by an etch tool to control etch process parameters such as etch time.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology system 100 may be configured for measurement of patterned wafers and/or unpatterned wafers. The metrology system may be configured as a LED inspection tool, solar inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A measurement system comprising:
   an illumination source configured to generate an amount of illumination light;
   one or more illumination optical elements configured to receive the amount of illumination light from the illumination source and project an illumination measurement beam to a specimen under measurement along an illumination beam path;
a detector configured to generate a plurality of output signals indicative of a response of the specimen to the incident illumination measurement beam;
one or more collection optical elements configured to collect an amount of collected light from the surface of the specimen and project a collection measurement beam from the specimen to the detector along a collection beam path;
a rotating optical polarizer element located in the illumination beam path, the collection beam path, or both;
a beam position sensor located in the illumination beam path, the collection beam path, or both, after the rotating optical polarizer element, wherein the beam position sensor generates output signals indicative of a location of the measurement beam;
an active beam compensating element located in the illumination beam path, the collection beam path, or both, between the rotating optical polarizer element and the beam position sensor; and
a computing system configured to:
receive the output signals indicative of the location of the measurement beam; and
communicate a command signal to the active beam compensating element that causes the active beam compensating element to adjust a location of the measurement beam toward a desired location as measured by the beam position sensor.

2. The measurement system of claim 1, wherein the active beam compensating element is a mirror element independently actuated in two rotational degrees of freedom.

3. The measurement system of claim 1, wherein the active beam compensating element is a lens element independently actuated in two translational degrees of freedom.

4. The measurement system of claim 1, wherein the active beam compensating element includes a pair of Risley prisms each independently actuated in a rotational degree of freedom.

5. The measurement system of claim 1, wherein the beam position sensor is a quadrature sensor having four optical sensors arranged in quadrature and an aperture centered at the intersection of the four optical elements.

6. The measurement system of claim 1, wherein the beam position sensor includes a plurality of light sensitive elements arranged about an axis of the illumination measurement beam, the collection measurement beam, or both.

7. The measurement system of claim 6, wherein the beam position sensor includes any of an array of charge coupled devices (CCD), an array of complementary metal oxide on silicon (CMOS) devices, a position sensitive detector (PSD) device, an array of photomultiplier tubes (PMT), and an array of photodiodes.

8. The measurement system of claim 1, wherein the beam position sensor includes:
a first beam position detector;
a focusing optical element; and
a beam diversion element disposed in the illumination optical path, the collection optical path, or both, that transmits a relatively large portion of the incident beam and reflects a relatively small portion of the incident beam toward the first beam position detector through the focusing optical element.

9. The measurement system of claim 8, wherein the beam position sensor also includes:
a second beam position detector; and
a beam splitting element, wherein the beam splitting element directs a first portion of the reflected beam toward the first beam position detector through the focusing element and a second portion of the reflected beam toward the second beam position detector.

10. The measurement system of claim 1, wherein the beam position sensor and the active beam compensating element are disposed in the collection beam path.

11. The measurement system of claim 1, wherein the beam position sensor and the active beam compensating element are disposed in the illumination beam path.

12. The measurement system of claim 1, wherein the measurement system is a spectroscopic ellipsometer.

13. The measurement system of claim 1, wherein the measurement system is configured to perform any of film metrology, composition metrology, critical dimension metrology, shape metrology, and overlay metrology.

14. The measurement system of claim 1, further comprising:
a rotary position sensor configured to measure a rotational position of the rotating optical polarizer element, the computing system further configured to:
communicate a command signal to the active beam compensating element that causes the active beam compensating element to adjust a location of the measurement beam toward a desired location of the measurement beam based on the measured rotational position of the rotating optical polarizer element.

15. A method comprising:
projecting a measurement beam to a specimen under measurement along an illumination beam path;
collecting an amount of collected light from the surface of the specimen in response to the incident measurement beam;
projecting the measurement beam from the specimen to a detector along a collection beam path;
generating a plurality of output signals indicative of a response of the specimen to the incident illumination measurement beam;
varying a rotational polarization of the measurement beam at a first location in an optical path of the measurement beam;
measuring a variation of position of the measurement beam at a second location in the optical path, wherein the second location in the optical path is located after the first location as the measurement beam propagates in the optical path;
adjusting a position of the measurement beam to reduce the variation of position of the measurement beam at a third location in the optical path, wherein the third location is located between the first location and the second location as the measurement beam propagates in the optical path.

16. The method of claim 15, wherein the adjusting of the position of the measurement beam to reduce the variation of position of the measurement beam is based on the measurement of the variation of position of the measurement beam.

17. The method of claim 15, further comprising:
measuring a rotational position of a rotating optical polarizer element that varies the rotational polarization of the measurement beam, wherein the adjusting of the position of the measurement beam to reduce the variation of position of the measurement beam is based on the measurement of the rotational position of the rotating optical polarizer element.

18. A measurement system comprising:
a rotating optical polarizer element located in a beam path of the measurement system;
a beam position sensor located in the beam path after the rotating optical polarizer element, wherein the beam position sensor generates output signals indicative of a location of the beam;
an active beam compensating element located in the beam path between the rotating optical polarizer element and the beam position sensor; and
a computing system configured to:
receive the output signals indicative of the location of the beam; and
communicate a command signal to the active beam compensating element that causes the active beam compensating element to adjust a location of the beam toward a desired location as measured by the beam position sensor.

19. The measurement system of claim 18, wherein the active beam compensating element is any of a mirror element independently actuated in two rotational degrees of freedom, a lens element independently actuated in two translational degrees of freedom, and a pair of Risley prisms each independently actuated in a rotational degree of freedom.

20. The measurement system of claim 18, wherein the beam position sensor includes:

a first beam position detector;
a focusing optical element;
a beam diversion element disposed in the beam path that transmits a relatively large portion of the incident beam and reflects a relatively small portion of the incident beam toward the first beam position detector through the focusing optical element;
a second beam position detector; and
a beam splitting element, wherein the beam splitting element directs a first portion of the reflected beam toward the first beam position detector through the focusing element and a second portion of the reflected beam toward the second beam position detector.

21. The measurement system of claim 18, further comprising:
a rotary position sensor configured to measure a rotational position of the rotating optical polarizer element, the computing system further configured to:
communicate a command signal to the active beam compensating element that causes the active beam compensating element to adjust a location of the beam toward a desired location of the beam based on the measured rotational position of the rotating optical polarizer element.

* * * * *